United States Patent
Sharma et al.

(10) Patent No.: US 12,226,226 B2
(45) Date of Patent: Feb. 18, 2025

(54) MEDICAL SYSTEM FOR SEAMLESS THERAPY ADJUSTMENT

(71) Applicant: Medtronic, Inc., Minneapolis, MN (US)

(72) Inventors: Vinod Sharma, Maple Grove, MN (US); Eduardo N. Warman, Maple Grove, MN (US); Shantanu Sarkar, Roseville, MN (US); Tommy D. Bennett, Shoreview, MN (US); Lindsay M. Streeter, Waconia, MN (US); Jennifer K. Bravinder, Denham Springs, LA (US)

(73) Assignee: Medtronic, Inc., Minneapolis, MN (US)

( * ) Notice: Subject to any disclaimer, the term of this patent is extended or adjusted under 35 U.S.C. 154(b) by 797 days.

(21) Appl. No.: 16/922,326

(22) Filed: Jul. 7, 2020

(65) Prior Publication Data

US 2020/0383634 A1 Dec. 10, 2020

Related U.S. Application Data

(63) Continuation of application No. 15/402,839, filed on Jan. 10, 2017, now abandoned.
(Continued)

(51) Int. Cl.
*A61B 5/00* (2006.01)
*A61B 5/0205* (2006.01)
(Continued)

(52) U.S. Cl.
CPC .......... *A61B 5/4839* (2013.01); *A61B 5/0205* (2013.01); *A61B 5/076* (2013.01);
(Continued)

(58) Field of Classification Search
None
See application file for complete search history.

(56) References Cited

U.S. PATENT DOCUMENTS

| 4,374,382 A | 2/1983 | Markowitz |
| 5,117,824 A | 6/1992 | Keimel et al. |

(Continued)

OTHER PUBLICATIONS

Cowie et al., "Development and Validation of an Integrated Diagnostic Algorithm Derived from Parameters Monitored In Implantable Devices for Identifying Patients at Risk for Heart Failure Hospitalization in an Ambulatory Setting", European Heart Journal (2013), 34, 2472-2480.
(Continued)

*Primary Examiner* — Matthew Kremer
(74) *Attorney, Agent, or Firm* — Mueting Raasch Group

(57) ABSTRACT

Methods and systems for seamless adjustment of treatment are disclosed. A determination is made as to whether to intervene with a patient's treatment. Implanted device memory data is acquired over a pre-specified time period. Risk status is determined from the device memory data. Another external device memory data is acquired over a pre-specified time period. A determination is made as to whether to adjust treatment of the patient in response to the risk status, the data acquired from the implanted device memory and the external device memory data.

19 Claims, 9 Drawing Sheets

Related U.S. Application Data

(60) Provisional application No. 62/435,181, filed on Dec. 16, 2016, provisional application No. 62/301,303, filed on Feb. 29, 2016.

(51) Int. Cl.
| | |
|---|---|
| *A61B 5/07* | (2006.01) |
| *G16H 20/10* | (2018.01) |
| *G16H 40/40* | (2018.01) |
| *G16H 40/63* | (2018.01) |
| *G16H 50/30* | (2018.01) |
| *A61B 5/021* | (2006.01) |
| *A61B 5/0215* | (2006.01) |
| *A61B 5/053* | (2021.01) |
| *A61J 1/00* | (2023.01) |
| *A61N 1/362* | (2006.01) |
| *A61N 1/365* | (2006.01) |
| *A61N 1/39* | (2006.01) |
| *G01G 19/44* | (2006.01) |
| *G16H 20/13* | (2018.01) |
| *G16H 40/67* | (2018.01) |

(52) U.S. Cl.
CPC ............ *A61B 5/686* (2013.01); *A61B 5/7275* (2013.01); *A61B 5/7282* (2013.01); *A61B 5/742* (2013.01); *G16H 20/10* (2018.01); *G16H 40/40* (2018.01); *G16H 40/63* (2018.01); *G16H 50/30* (2018.01); *A61B 5/021* (2013.01); *A61B 5/0215* (2013.01); *A61B 5/053* (2013.01); *A61B 5/4842* (2013.01); *A61B 5/4848* (2013.01); *A61B 5/4878* (2013.01); *A61B 5/6869* (2013.01); *A61B 5/6876* (2013.01); *A61B 2560/0475* (2013.01); *A61J 1/00* (2013.01); *A61N 1/3627* (2013.01); *A61N 1/36521* (2013.01); *A61N 1/36564* (2013.01); *A61N 1/3956* (2013.01); *G01G 19/44* (2013.01); *G16H 20/13* (2018.01); *G16H 40/67* (2018.01)

(56) References Cited

U.S. PATENT DOCUMENTS

| | | |
|---|---|---|
| 5,545,186 A | 8/1996 | Olson et al. |
| 5,755,736 A | 5/1998 | Gillberg et al. |
| 6,970,742 B2 | 11/2005 | Mann et al. |
| 7,577,475 B2 | 8/2009 | Cosentino et al. |
| 7,986,994 B2 | 7/2011 | Stadler et al. |
| 8,255,046 B2 | 8/2012 | Sarkar et al. |
| 8,271,080 B2 | 9/2012 | Thompson et al. |
| 8,343,059 B1 | 1/2013 | Koh |
| 8,419,650 B2 | 4/2013 | Cosentino et al. |
| 8,585,604 B2 | 11/2013 | Bennett et al. |
| 9,675,270 B2 | 6/2017 | Sarkar |
| 9,713,701 B2 | 7/2017 | Sarkar et al. |
| 9,814,424 B2 | 11/2017 | Zhang et al. |
| 9,943,234 B2 | 4/2018 | Dalal et al. |
| 2003/0199813 A1* | 10/2003 | Struble ................ A61B 5/0031 600/485 |
| 2004/0147969 A1 | 7/2004 | Mann et al. |
| 2008/0077440 A1 | 3/2008 | Doron |
| 2008/0262360 A1* | 10/2008 | Dalal .................. A61N 1/3627 600/484 |
| 2010/0030293 A1* | 2/2010 | Sarkar .................... A61B 5/021 607/18 |
| 2012/0032243 A1 | 2/2012 | Kutsukake et al. |
| 2013/0085399 A1 | 4/2013 | Bennett et al. |
| 2013/0340758 A1* | 12/2013 | Schindhelm ........... G16H 50/20 128/204.23 |
| 2016/0361026 A1 | 12/2016 | Sarkar et al. |
| 2017/0164845 A1 | 6/2017 | Campbell et al. |

OTHER PUBLICATIONS

International Search Report and Written Opinion from International Application No. PCT/US2017/019300, dated Jun. 1, 2017, 15 pages.

Ritzema et al., "Physician-Directed Patient Self-Management of Left Atrial Pressure in Advanced Chronic Heart Failure", http://circ.ahajournals.org., pp. 1086-1095, Feb. 22, 2010.

\* cited by examiner

MEDICAL SYSTEM FOR SEAMLESS THERAPY ADJUSTMENT

CROSS-REFERENCE TO RELATED APPLICATIONS

This application is a continuation of U.S. application Ser. No. 15/402,839, filed Jan. 10, 2017 which claims the benefit of U.S. Provisional Application No. 62/301,313, filed on Feb. 29, 2016 and U.S. Provisional Application No. 62/435,181 filed on Dec. 16, 2016. The disclosure of the above applications are incorporated herein by reference in their entirety.

TECHNICAL FIELD

The present disclosure relates to a medical system, and, more particularly, to a medical system configured to determine whether to intervene with a patient's treatment.

BACKGROUND

Chronic heart failure (CHF) is a serious condition that occurs when a heart is unable to consistently pump blood at an adequate rate. To improve the ability of the heart to pump blood, CHF patients may require an implantable medical device (IMD). IMDs such as implantable cardioverter defibrillators (ICDs) or pacemakers are capable of delivering cardiac resynchronization therapy for improving a CHF patient's heart function. Despite using IMDs to improve heart function, CHF patients may progressively deteriorate, as evidenced by weight gain, change in blood pressure, malaise, fatigue, swelling, fainting, and/or palpitations.

Patient data are obtained in a variety of ways. Typically, a patient directly conveys health data to medical personnel during an office visit. Some data may be automatically generated and sent over the Internet to a computer system or health care system. For example, electronic weight scales are configured to weigh a patient and then automatically transmit that data to the health care system.

In response to the collected data, healthcare systems can respond in a variety of ways. Some healthcare systems are able to generate health alerts based upon data detected by an IMD. One exemplary healthcare system relates to US Patent Application US 2010-0030293 A1 to Sarkar et al. that is capable of generating alerts for a patient to seek medical treatment in response to detected information. For example, a medical device may detect worsening heart failure in the patient based on a diagnostic parameter. Upon detecting worsening heart failure, the medical device may, for example, provide an alert that enables the patient to seek medical attention before experiencing a heart failure event.

While numerous healthcare systems are able to automatically notify health care workers of potential health issues such as that which is described in US Patent Application US 2010-0030293 A1 to Sarkar et al., a healthcare system typically requires a physician's input to adjust therapy (i.e. medication) delivered to a patient. It is desirable to develop a healthcare system that is able to seamlessly respond to a patient's deteriorating health conditions without directly contacting a physician.

SUMMARY OF THE DISCLOSURE

Methods and systems are disclosed for seamless adjustment of therapy delivered to a patient. Therapy (e.g. medication) is adjusted without direct real time input by the physician. Instead, the computer system causes preauthorized prescriptions from the physician to be implemented based upon one or more conditions. After one or more conditions are met, a nurse or a computer system sends a message to the patient that an adjustment is needed to their prescription medication. In the scenario involving a computer sent message, the message transmission can be performed automatically upon meeting one or more conditions. The patient has the medication stored within his environment (e.g. home, office etc.) and can take the newly prescribed medication such as non-addictive medication, incremental dose of medication and/or addition/removal of medication.

To determine whether to intervene with the therapy delivered to a patient, a series of steps are implemented. For example, data are acquired from an implanted device memory over a pre-specified time period. A patient's heart failure (HF) risk status is then determined from the device memory data (e.g. weight, symptoms and/or blood pressure). Data is acquired from the external device, another external device memory and/or an implantable medical device over a pre-specified time period. A determination is then made as to whether to adjust treatment of the patient in response to a patient's heart failure (HF) risk status, the data acquired from the implanted device memory, and the external device memory data.

The present disclosure achieves numerous benefits over conventional healthcare systems. For example, the healthcare system is configured to adjust therapy without directly contacting the physician immediately and/or in real-time before adjusting the therapy. By adjusting therapy without first contacting the physician, time spent by the physician, the patient and the patient's caretaker are reduced compared to conventional health care systems that requires the patient to physically visit the doctor whenever the patient's diuretics require adjustment. Additionally, the patient will be administered the proper medication in a more timely fashion thereby reducing or avoiding worsening HF condition.

DETAILED DESCRIPTION

Figure 1:
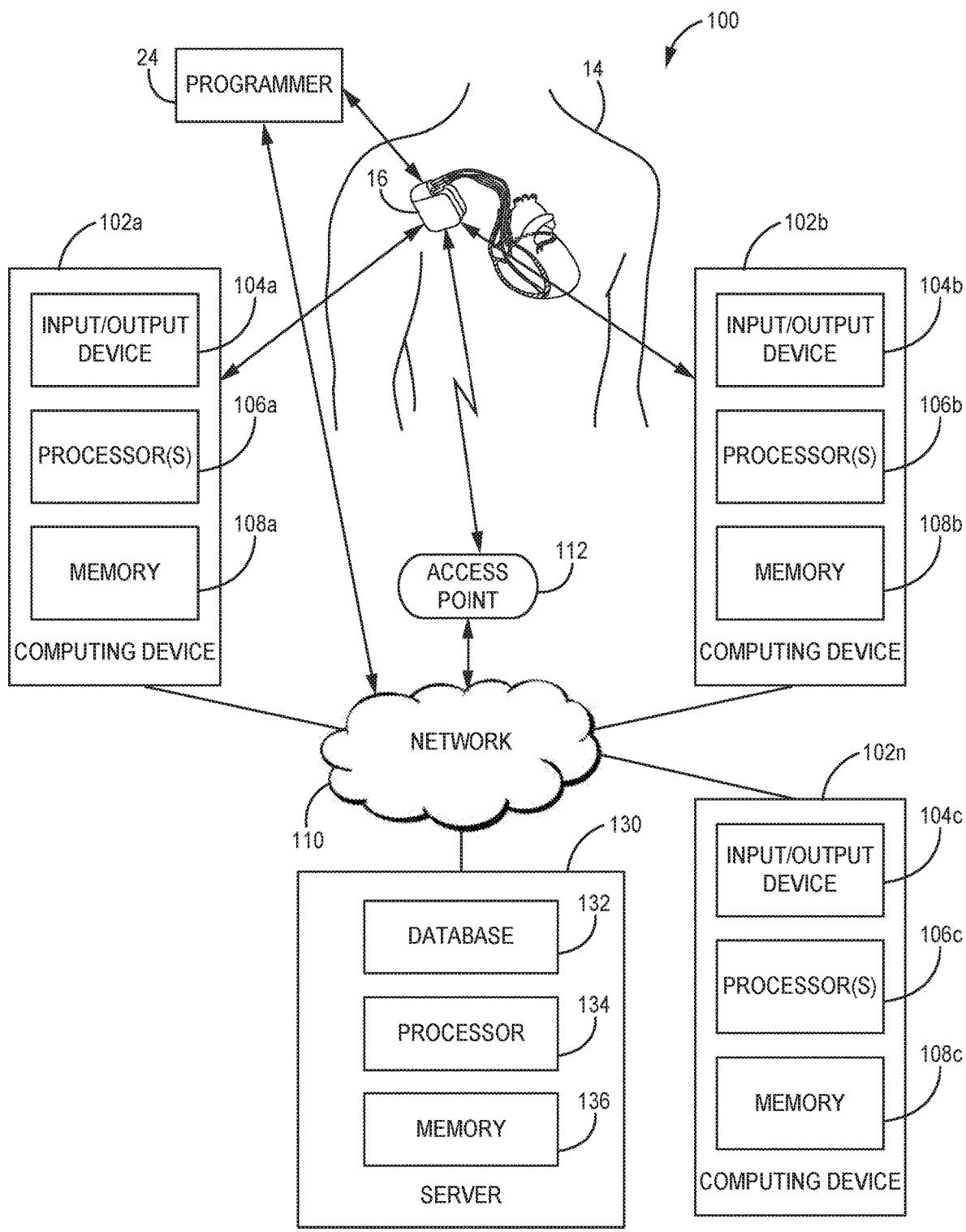
FIG. 1 is a block diagram illustrating an example computer system that includes an external device and one or more computing devices that are coupled to the IMD and programmer shown in FIG. 1 via a network.
Figure 2:
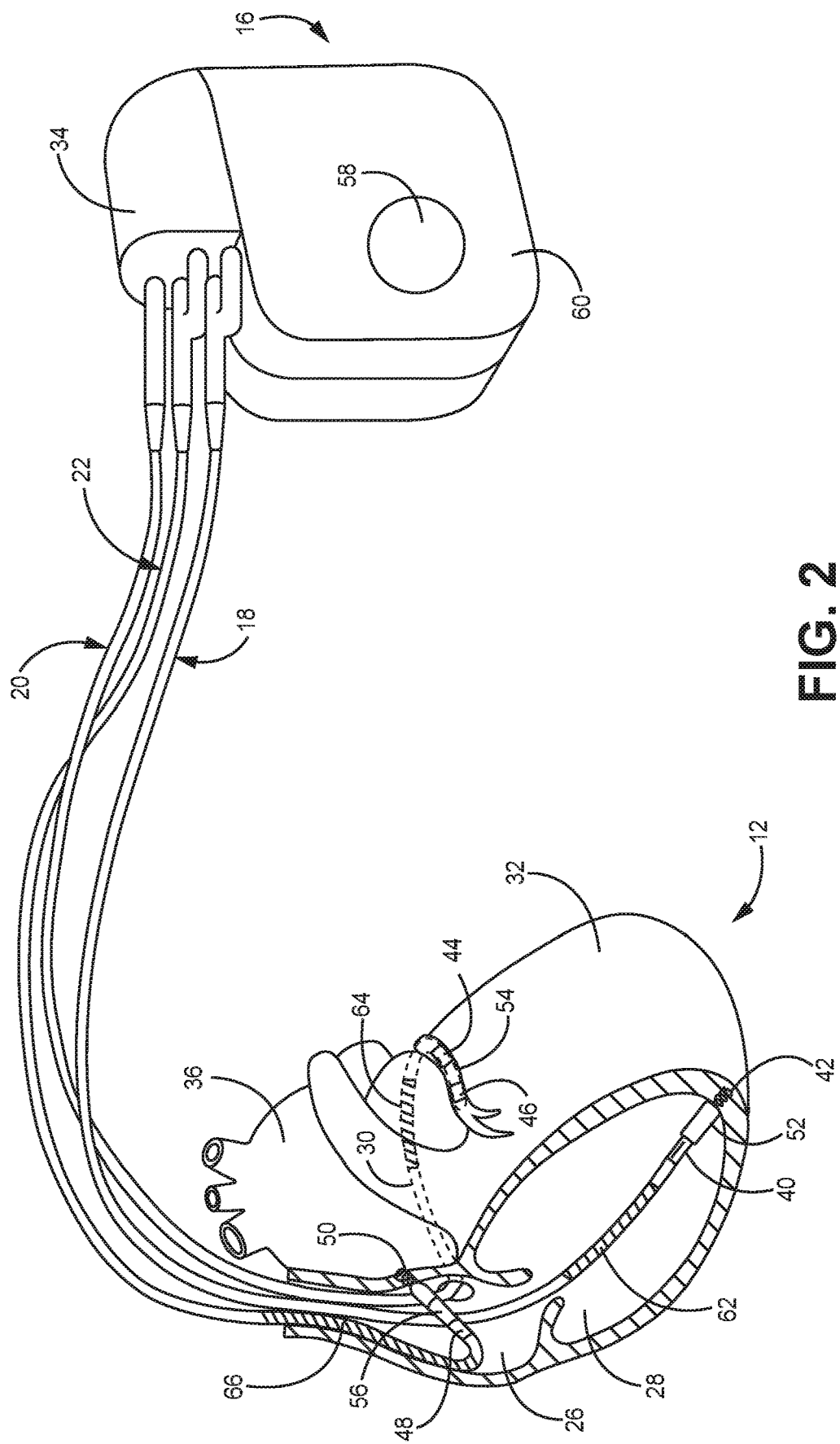
FIG. 2 is a diagram of the exemplary IMD shown in FIG. 1.
Figure 3:
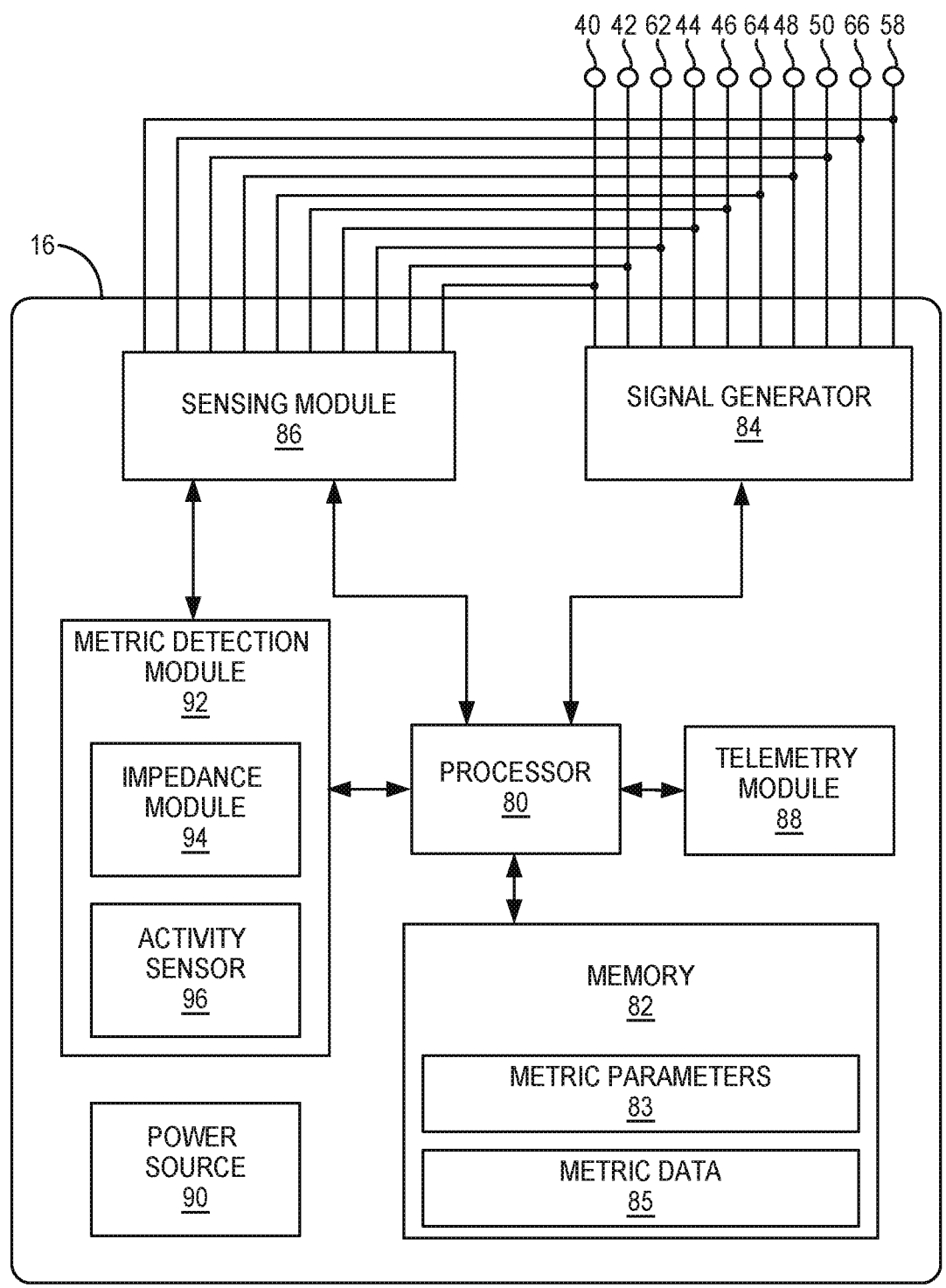
FIG. 3 is a functional block diagram of the exemplary IMD shown in FIG. 1.

Exemplary systems, methods, and interfaces shall be described with reference to FIGS. 1-9. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others. FIGS. 1-3 disclose a system for intervening into the therapy delivered to the patient while FIG. 4 discloses a flow diagram, controlled by the system, for an intervention to modify the therapy delivered to a patient.

FIG. 1 is a block diagram illustrating an exemplary computer system 100 that can seamlessly trigger the adjustment of a patient's treatment plan without directly communicating with the patient's physician any time after the treatment plan has been sent to a centralized communication center for storage or stored into a memory of a computing device. The treatment plan, stored at the centralized communication center or in the memory of a server, can comprise one or more rounds of medication (e.g., a first round of medication, a second round of medication etc.). Generally, adjusting treatment of the patient depends on the patient's risk of a HF event, and data acquired from IMD 16, computing devices 102a-n and/or programmer 24. A HF event is when a patient was admitted to the hospital for worsening HF or the patient has received Intravenous HF therapy (e.g. IV diuretics/vasodilators), ultrafiltration at any settings including an emergency department, ambulance, observation unit, urgent care, HF/Cardiology Clinic or the patient's home. Communication of the adjusted treatment can be delivered either electronically or via nurse to the patient.

Computer system 100 includes one or more computing devices 102a-102n, a programmer 24, a server 130, a network 110, and access point 112. Network 110 may generally be used to transmit information or data (e.g., physiological data, risk level data, recovery data) between IMD 16 to other external computing devices 102a-c. However, network 110 may also be used to transmit information from IMD 16 to an external computing device (e.g. CARELINK®). Exemplary computer systems and/or features that can implement the present disclosure include U.S. Pat. No. 8,585,604 to Bennett et al., U.S. Pat. No. 6,970,742 to Mann et al., Ritzema et al, Physician-Directed Patient Self-Management of Left Atrial Pressure in Advanced Chronic Heart Failure, Circulation, 2010, U.S. Pat. No. 7,577,475 to Cosentino et al, —System, method, and apparatus for combining information from an implanted device with information from a patient monitoring apparatus, 2009, the disclosure of each are incorporated by reference in their entirety.

IMD 16 may use its telemetry module 88, described below relative to FIG. 3, to communicate with computing devices 102a-n ("n" being any whole number of computing devices), server 130, programmer 24. Typically, a wireless connection is employed. In one example of FIG. 1, access point 110, programmer 24, external device 102n, and computing devices 102a-102n can be interconnected, and able to communicate with each other, through network 112. In some cases, one or more of access point 110, programmer 24, external device 102n, and computing devices 102a-102n may be coupled to network 112 through one or more wireless connections.

Figure 7:
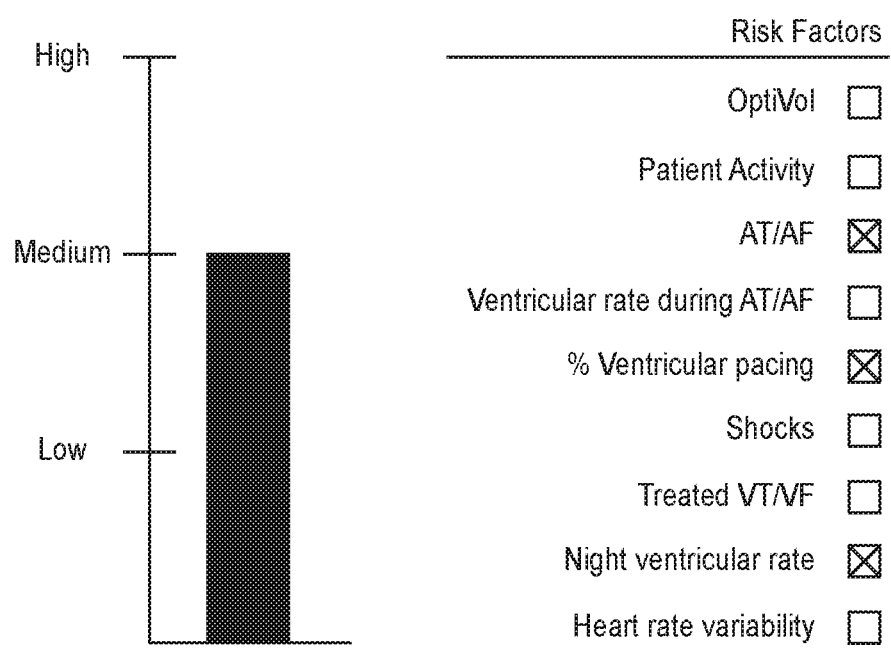
FIG. 7 depicts medium risk status relative to a set of exemplary risk factors.

Another example of a computing device 102n may be a patient's medication or drug dispenser 102, as shown in FIG. 7. The computerized drug dispenser 102 includes a set of compartments, in which each compartment 103a-d stores one or more medications at a prescribed dosage. The drug dispenser if further configured to receive instructions from the server to ensure that the patient has access to the correct medication and/or dosage of medication. Once the server determines a medication for a patient needs to be adjusted, the server automatically signals the computing device 102n to automatically adjust delivery of the medication. For example, assume that the patient requires a reduced dosage of a medication. The server signals the computing device 102n to adjust the dosage delivered to a patient. The computing device 102n automatically switches from the first to a second dosage compartments for drug delivery. The medication delivery device rotates from the first dosage compartment that stores a first dosage to the second dosage compartment that stores a second dosage for delivery to the patient. The medication delivery device automatically notifies the patient there has been a modification in his or her dosage. The medication delivery device then automatically notifies the patient to take the medication during the day. The drug is automatically dispensed to the patient at the proper dosage. The dispenser can be set to automatically lock drug delivery once the proper dosage has been delivered.

IMD 16, programmer 24, external device 102n, and computing devices 102a-102n may each comprise one or more processors, such as one or more microprocessors, DSPs, ASICs, FPGAs, programmable logic circuitry, or the like, that may perform various functions and operations, such as those described herein. Each processor can be configured to perform some type of analog to digital conversion (ADC) so that signals can be compared to some threshold. The signal can be filtered before or after digitizing the signal. Other applicable signal processing may also be applied.

Computing devices 102a-102n may comprise devices such as servers, computers, weight scales, portable blood pressure machines, biometric data collecting device, a computer, a symptom assessment system, a personal digital assistant (e.g. cell phone, iPad, or the like). In some examples, computing devices 102a-n may generate data that are used by server to perform any of the various functions or operations described herein, e.g., generate a heart failure risk status based on the patient metric comparisons or create patient metrics from the raw metric data. Computing devices 102a-n include input/output device 104c, processor 106b and memory 108c.

Each computing device includes an input/output device 104a-c, a processor, 106a-c, and memory 108a-c. Input/output device 116 includes input devices such as a keyboard, a mouse, voice input, sensor for weight, etc. and output device includes graphical user interfaces, printers and other suitable means. Processor 106a-c or 134 includes any suitable processor. The processor 134 can be configured to perform some type of analog to digital conversion so that signal can be compared to some threshold. Processor 134 is configured to perform a variety of functions such as calculations, accessing data from memory performing comparisons, setting the start and end dates for each evaluation period etc. The evaluation period serves as an evaluation window that encompasses data, acquired from each patient, that are within the boundaries (i.e. start and end times).

Exemplary calculations performed by processor 106a-c can be calculating risk of a heart failure event for each evaluation period.

Memory 108a-c may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. Memory 108a-c stores data. Exemplary data stored in memory 108a-c includes heart failure patient data, heart failure prospective risk data, intracardiac or intravascular pressure, activity, posture, respiration, thoracic impedance, impedance trend, risk of hypervolemia or hypovolemia etc. Evaluation period start and end times are also stored in memory. Heart failure patient data includes data observations (e.g. data sensed from sensors that cross a threshold). Additionally, evaluation period data is also stored in memory 108a-c. For example, the start and end dates of the evaluation period data is stored in memory 108a-c.

Programmer 24 can include any appropriate programming system, including one generally known to those skilled in the art, such as the Medtronic CARELINK™ programmer, sold by Medtronic, Plc. of Minneapolis, MN Programmer 24 may communicate wirelessly with IMD 16, such as using RF communication or proximal inductive interaction. This wireless communication is possible through the use of telemetry module, which may be coupled to an internal antenna or an external antenna. An external antenna that is coupled to programmer 24 may correspond to the programming head that may be placed over heart. The telemetry module may also be configured to communicate with another computing device via wireless communication techniques, or direct communication through a wired connection. Examples of local wireless communication techniques that may be employed to facilitate communication between programmer 24 and another computing device include RF communication according to the 102.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, programmer telemetry module (not shown) may transmit an interrogation request to telemetry module of IMD 16. Accordingly, the telemetry module may receive data (e.g. diagnostic information, real-time data related to absolute intrathoracic impedance that may be indicative of hypervolemia or hypovolemia, etc.) or diagnostic information selected by the request or based on already entered patient status to IMD 16. The data may include patient metric values or other detailed information from telemetry module of IMD 16. The data may include an alert or notification of the heart failure risk level from the telemetry module of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment (e.g. testing to confirm worsening HF etc.). In response to receiving the alert, the user interface may display the alert to the healthcare professional regarding the risk level or present an instruction to patient 14 to seek medical treatment.

Either in response to heart failure data, e.g., the risk level or patient metrics, or requested heart failure information, the user interface for a computing device or programmer 24 may present the patient metrics, the heart failure risk level, or recommended treatment (e.g. medication) to the user. In some examples, the user interface may also highlight each of the patient metrics that have exceeded the respective one of the plurality of metric-specific thresholds. In this manner, the user may quickly review those patient metrics that have contributed to the identified heart failure risk level.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein.

In another example, access point 110 may be a LINQ™ device co-located within the patient and configured to sense, record and transmit data to network 110. Alternatively, SEEQ™, configured for monitoring, maybe attached to the skin of the patient. In another example, access point 110 may include a home-monitoring unit that is located within patient 14 and that may monitor the activity of IMD 16. LINQ™ and SEEQ™ commercially available from Medtronic, Inc. located in Minneapolis, MN may also be used as access point 110. An example of such a LINQ™ may be seen with respect to U.S. Pregrant Publication No. 2016-0310031 A1 filed Apr. 20, 2016, and assigned to the assignee of the present invention, the disclosure of which is incorporated by reference in its entirety herein.

Server 130 can be located at a centralized communication center such as at Cardiocom®. Server 130 is configured to perform complex computations for a large group of patients and provides secure storage in memory 136 for archival of information (e.g., patient metric data, heart failure risk levels, weight, blood pressure etc.) setup in a database 132 that has been collected and generated from IMD 16, programmer 24 and/or external devices. Exemplary medium and high risk calculations are shown and described in US 2016-0361026 A1 (U.S. application Ser. No. 13/391,376) entitled METHOD AND APPARATUS FOR MONITORING TISSUE FLUID CONTENT FOR USE IN AN IMPLANTABLE CARDIAC DEVICE and US2012032243 (U.S. application Ser. No. 12/914,836 filed Oct. 28, 2010), entitled HEART FAILURE MONITORING AND NOTIFICATION and assigned to the assignee of the present invention, the disclosure of which is incorporated by reference in its entirety herein.

Figure 8:
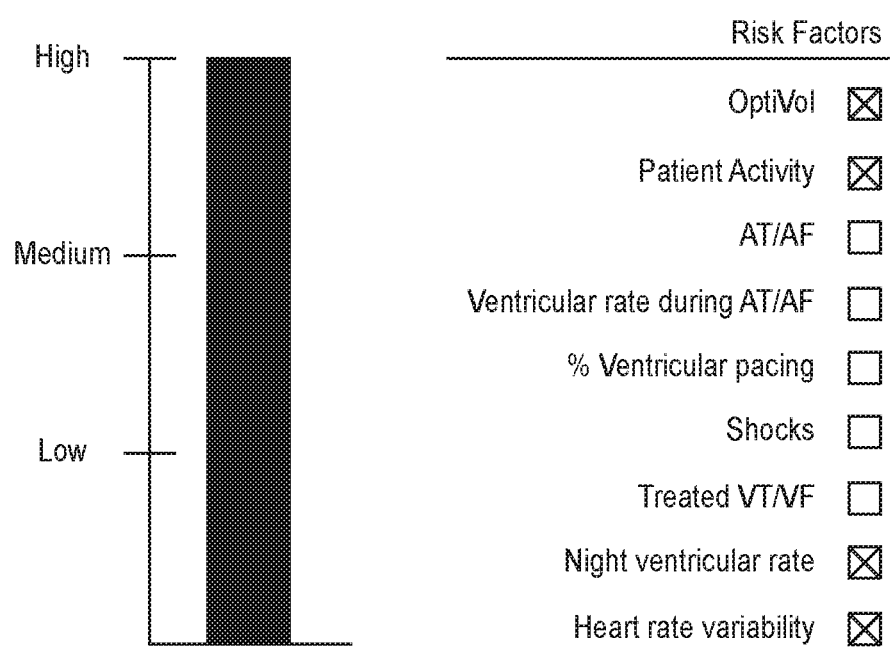
FIG. 8 depicts high risk status relative to a set of exemplary risk factors.
Figure 9:
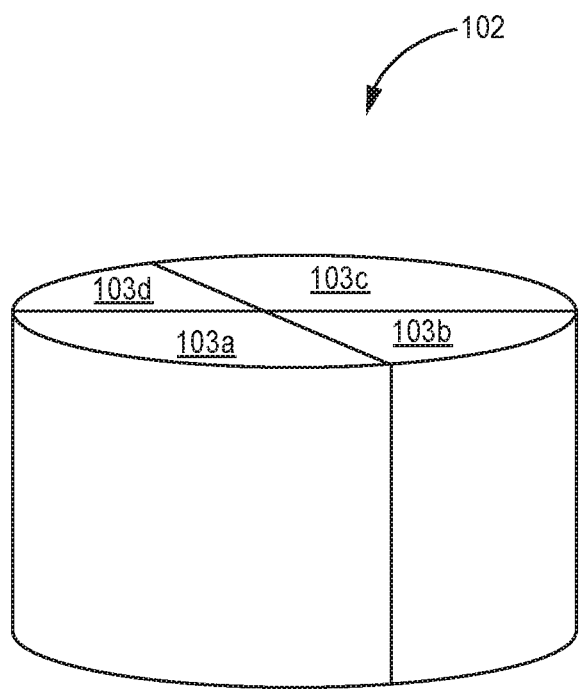
FIG. 9 is a block diagram of a patient's medication dispenser.

Examples of medium and high risk status are presented in FIGS. 7-8. Medium risk status, for example, may involve one or more conditions such as AT/AF burden exceeding a threshold value (>6 hours/day), low % V pacing and high night heart rate (>85 bpm). High risk status, for example, may involve one or more conditions such as high OptiVol™/impedance index (>60 ohm-days), patient activity (<1 hour/day), high night heart rate (>85 bpm) and low HRV (<60 ms).

Memory 136 stores a set of diagnostic metrics indicative of worsening heart failure for each patient. Diagnostic metrics or metrics can include a variety of data. Exemplary data, shown in FIG. 5, includes (1) impedance trend index commercially available in IMDs from Medtronic Plc., located in MN), (2) intrathoracic impedance, (3) atrial tachycardia/atrial fibrillation (AT/AF) burden, (4) mean ventricular rate during AT/AF, (5) patient activity, (6) ventricular (V) rate, (7) day and night heart rate, (8) percent CRT pacing, and/or (9) number of shocks. The impedance index is an indicator of the amount of fluid congestion experienced by the patient. The impedance index is the difference between an impedance measured during real time using IMD 16 and a reference impedance, that can be continuously updated, established by the IMD 16 or during another visit to the physician. The impedance index is described in greater detail with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein.

Heart rate variability (HRV) is a marker of autonomic tone and has been shown to provide prognostic information for mortality risk. A decrease in HRV is associated with increased sympathetic tone. Using HRV device diagnostic data, patients with low HRV (<100 ms) are at a higher combined risk of death and hospitalization. Patients with HRV<50 ms exhibit an even higher risk than those with HRV in the range of 50-100 ms.

Similar to HRV, elevated heart rate is a marker of elevated sympathetic tone and has been shown to have prognostic value for worsening HF. Night Heart Rate (NHR), measured between midnight and 4 AM, can be a better metric than the day time heart rate. Day time heart rate can be affected by varying activity level (e.g. rest and exercise). Patients with high NHR (75±25 bpm) typically experience higher risk of being hospitalized or dying than those who had low NHR (73±11 bpm)[

Additionally, declining patient activity is associated with worsening HF status and can potentially be of value for predicting HF hospitalization. Declining patient activity can be determined by a variety of activity devices such as a FITBIT, cellphone etc.

Combination variables (e.g. combining pacing and arrhythmia related information) can also be used to evaluate worsening HF risk. For example, one of the components of combination variable is substantial decrease (>8%) in CRT pacing, which is associated with high HF events. A decline in CRT pacing can occur because of rapid conduction during AF. Thus, mean ventricular rate 90 bpm and atrial fibrillation (AF) burden 6 hours/day and shocks delivered to Ventricular Fibrillation/Ventricular Tachycardia (VT/VF) can also be components of the combination variable.

IMD 16, programmer 24, and/or computing devices a-n may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

Network 110 may comprise a local area network, wide area network, or global network, such as the Internet. In some cases, programmer 24 or external server 130 may assemble the diagnostic data, heart failure data, prospective heart failure risk data or other suitable data in web pages or other documents for viewing by and trained professionals, such as clinicians, via viewing terminals associated with computing devices 120. The system 100 of FIG. 1 may be implemented, in some aspects, with general network technology and functionality similar to that provided by the Medtronic CareLink® Network developed by Medtronic, Plc., of Minneapolis, MN FIG. 2 is an enlarged view of IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient. In general, the techniques described in this disclosure may be implemented by any medical device, e.g., implantable or external, that senses a signal indicative of cardiac activity, patient 14 activity, and/or fluid volume within patient 14. As one alternative example, the techniques described herein may be implemented in an external cardiac monitor that generates electrograms of heart 12 and detects thoracic fluid volumes, respiration, and/or cardiovascular pressure of patient 14.

Leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 100 may additionally or alternatively include one or more leads or lead segments (not shown in FIG. 2) that deploy one or more electrodes within the vena cava, or other veins. Furthermore, in some examples, system 100 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped.

IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use intrathoracic impedance to create a fluid index. As the fluid index increases, more fluid is being retained within patient 14 and heart 12 may be stressed to keep up with moving the greater amount of fluid. Therefore, this fluid index may be a patient metric transmitted in diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Pat. No. 8,255,046 to Sarkar et al., entitled, "DETECTING WORSENING HEART FAILURE BASED ON IMPEDANCE MEASUREMENTS," which published on Feb. 4, 2010 and is incorporated herein by reference in its entirety.

Whether a patient begins to experience or is experiencing HF symptoms is based upon a variety of parameters that can change over time. Exemplary parameters capable of changing over time includes the patient's weight (i.e. extreme weight loss), hypotension, syncope, pre-syncope, all of which can be uploaded to the system 100 on a periodic basis (e.g. daily, weekly, monthly etc.) from the patient's computer and/or user device 102*a-n*.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRI- CAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. Processor 80 detects data (e.g. data observations etc.) at an IMD16 check and/or interrogation time point. Data is sensed based on signals from sensing module 86. Additionally, cardioversion or defibrillation shock can be determined to be needed based upon sensed data, and processor 80 may control the amplitude, form and timing of the shock delivered by signal generator 84.

Memory 82 is configured to store data. Exemplary data can be associated with a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric. Preferred metrics include an (1) impedance trend index (also referred to as OPTIVOL® commercially available in IMDs from Medtronic Inc., located in MN), (2) intrathoracic impedance, (3) atrial tachycardia/atrial fibrillation (AT/AF) burden, (4) mean ventricular rate during AT/AF, (5) patient activity, (6) V rate, (7) day and night heart rate, (8) percent CRT pacing, and/or (9) number of shocks. Impedance trend index is described with respect to U.S. patent Ser. No. 10/727,008 filed on Dec. 3, 2003 issued as U.S. Pat. No. 7,986,994, and assigned to the assignee of the present invention, the disclosure of which is incorporated by reference in its entirety herein. Other suitable metrics can also be used. For example, a reference or baseline level impedance is established for a patient from which subsequently acquired raw impedance data is compared. For example, raw impedance can be acquired from the electrodes (e.g. RV coil to Can) and compared to the reference impedance. Baseline impedance can be derived by averaging impedance over a duration of 7 days (1-week) to 90 days (3-months).

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of about 60 □-days an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate.

Metric data 85 is a portion of memory 82 that may store some or all of the patient metric data that is sensed and/or detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. In one or more other embodiments, memory can be configured for long term storage of data. Processor 80 may access metric data when necessary to retrieve and transmit patient metric data and/or generate heart failure risk levels. In addition, metric data 85 may store any and all data observations, heart failure risk levels or other generated information related to the heart failure risk of patient 14. The data stored in metric data 85 may be transmitted as part of diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate diagnostic data, e.g., data that indicates a threshold has been crossed, risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure status or that patient 14 is at risk for worsening HF. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of disclosed herein to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being effectively delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements. In one or more other embodiments, low effective CRT amounts or effective V-pacing for CRT pacing can also be used as indicators of improved therapy efficacy.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional submodules or sub-routines that detect and monitor other patient metrics used to monitor patient 14 and/or generate the HF risk level. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or raw intrathoracic impedance which is subsequently compared to a reference impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate risk levels (e.g. risk of, or exhibiting hypervolemia, hypovolemia, HFH risk level) based upon the patient metrics sensed, detected, and stored in metric data 85 of memory 82. For example, processor 80 may continually update the risk level as metric detection module 92 updates each patient metric. In other examples, processor 80 may periodically update the HFH risk level according to an updating schedule. In one or more other embodiments, the total number of data observations that exceed or cross a threshold within a pre-specified period of time can be used to determine the risk of a heart failure event or worsening HF.

As described above, processor 80 may provide an alert to a user, e.g., of programmer 24, regarding the data from any patient metric and/or the HFH risk level. In one example, processor 80 may provide an alert with the HFH risk level when programmer 24 or another device communicates with IMD 16. Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Plc. of Minneapolis, MN, or some other network linking patient 14 to a clinician. In this manner, a computing device or user interface of the network may be the external computing device that delivers the alert, e.g., patient metric data. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device.

Figure 4:
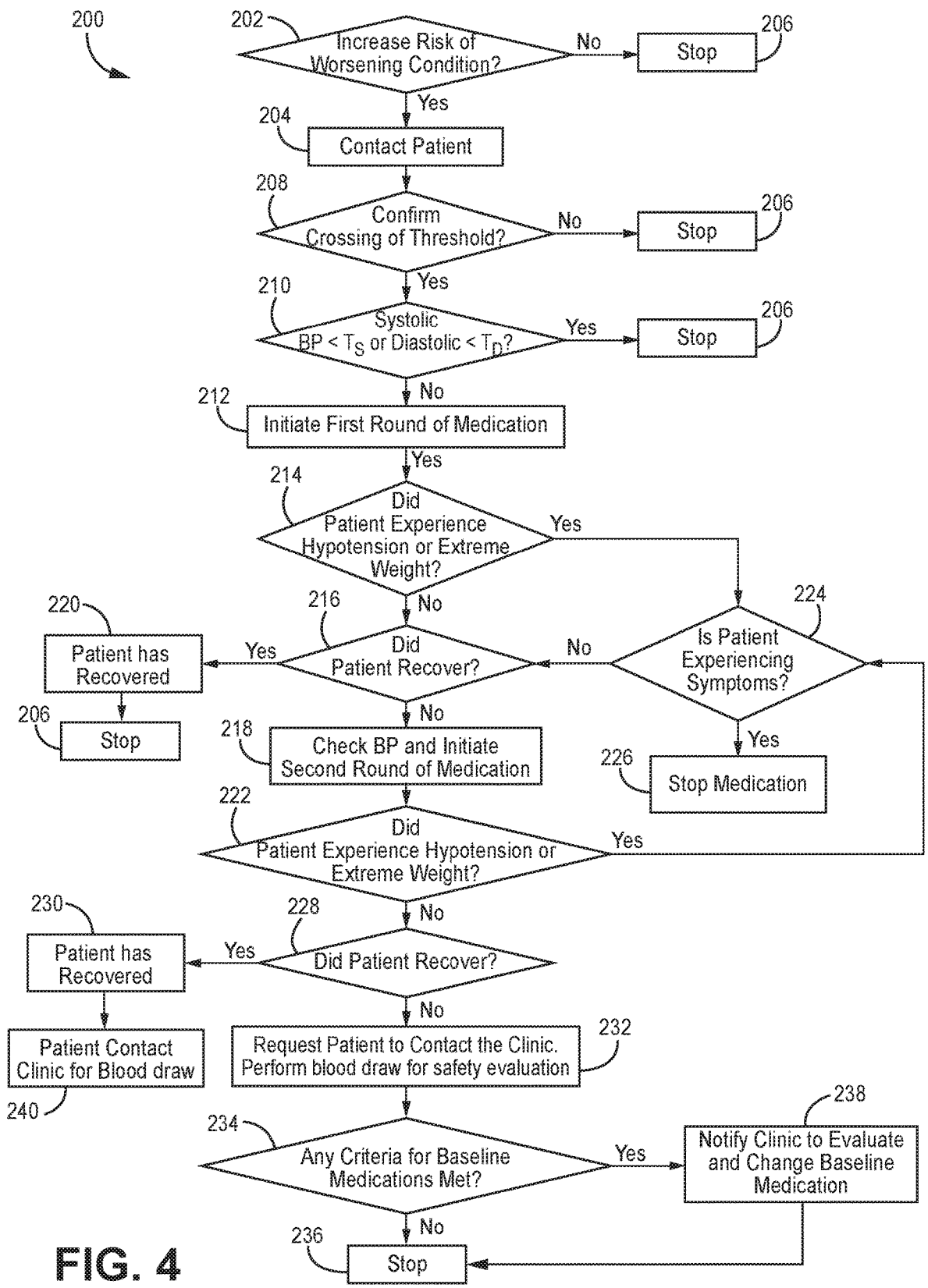
FIG. 4 is a flow diagram of an exemplary symptom management intervention process controlled by a medical system that can cause one or more adjustments to therapy that is being delivered to a patient.
Figure 5:
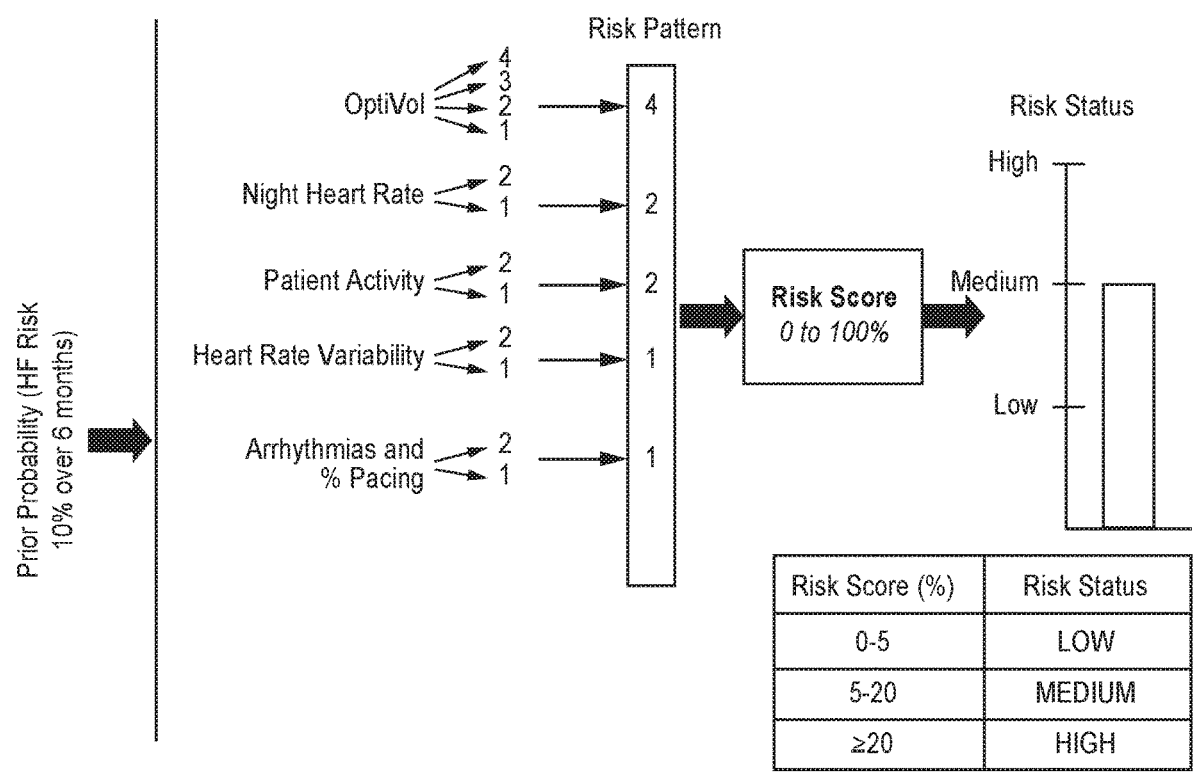
FIG. 5 is a block diagram of integrated diagnostics related to risk status.

System 100 controls implementation of an intervention method 200, depicted in a flow diagram of FIG. 4, to seamlessly adjust patient's therapy (e.g. medication). At block 202, a determination is made as to whether the patient is experiencing increased risk of worsening HF condition. Risk of worsening HF condition is calculated using data such as data acquired from IMD 16. For example, data, acquired from the IMD 16, shows a threshold level is crossed. The data, showing an exceedance or that a threshold has been crossed, is transmitted to server 130. Other data that may be useful for determining risk of worsening condition can be obtained from computing devices 102*a-n*.

Server 130 combines all of the diagnostic data in order to determine a patient's HF risk. Numerous methods exist for determining a patient's risk of experiencing a HF event. One methodology uses a Bayesian Belief Probabilistic model to categorize patients into three risk categories—low, medium and high. Exemplary medium and high risk calculations are shown and described in US2012032243, entitled HEART FAILURE MONITORING AND NOTIFICATION and assigned to the assignee of the present invention, the disclosure of which is incorporated by reference in its entirety herein. One or more other embodiments that may be employed is directed to Martin R. Cowie et al., Development and Validation Of An Integrated Diagnostic Algorithm Derived From Parameters Monitored in Implantable Devices For Identifying Patients At Risk For Heart Failure Hospitalization In An Ambulatory Setting, European Heart Journal (2013) 34, 2472-2480 doi:10.1093/eurheartj/eht083, the disclosure of which is incorporated by reference in its entirety herein.

Briefly, the present disclosure uses a set of variables as input. Exemplary set of variables include thoracic impedance, activity, heart rate variability, heart rate, and a combination variable based on arrhythmia and shock related information collected by the IMD 16. Intrathoracic impedance (e.g. OptiVol®) is a useful measure of a patient's HF status because HF status typically worsens when atrial filling pressure increases thereby causing retention of fluid in the pulmonary circulation. If sustained over time, fluid can infiltrate into interstitial space leading to worsening pulmonary congestion. Since blood and interstitial fluid are highly conductive, fluid accumulation in the pulmonary system leads to a reduction in thoracic impedance.

After a HF risk status of the patient is calculated, the HF risk status data is then stored into memory 136 of the server 130. If a patient's risk is deemed high, the patient automatically falls within the scope of worsening condition. Worsening HF condition also occurs in medium risk patients who exhibit sign/symptoms present (e.g. weight gain, dyspnea etc.) that may be acquired from external biometric data devices.

After evaluating patient information, a determination can be made that the risk alert from the patient is not specific to worsening HF. In this scenario, the NO path from block 202 continues from block 206 in which the method 200 is terminated and the process returns to monitoring for worsening HF conditions in the patient. The YES path continues from block 202 to block 204 in which medical personnel (e.g. nurse located a central communication center etc.) communicates with the patient through electronic communication (e.g. email, text messaging, phone call or mail) in order to determine whether the patient's worsening condition is HF related. The medical personnel may present one or more questions to the patient. For example, the patient may be asked if he or she had undergone a recent surgery. At block 208, a determination is made as to whether the threshold crossing is related to HF. A threshold crossing can be confirmed as a HF occurrence based upon information provided by the patient. Typically, to confirm whether the worsening condition is HF related, the patient is asked to respond to the questions presented below. The questions can be posed by a nurse located near the central server 130 or electronically presented to the patient via server 130 to a GUI associated with a computing device 102*a-n*. Exemplary questions that can be posed to a patient include the following:

1. Has the CRT-D device or lead been changed?
2. Has the patient been discharged from the hospital within the last two days?
3. Did the patient receive intravenous fluids for more than 1 day while in the hospital?
4. Did the patient experience chills, shivering, shaking or muscle aches?
5. Has the patient been treated for a chronic obstructive pulmonary disease (COPD) exacerbation?
6. Did any changes occur to baseline diuretic medication in the past 3 weeks?

If the response to anyone of the questions is "yes", the threshold crossing is deemed to not be a HF occurrence. All other occurrences may be deemed HF related.

If a threshold has been confirmed as having been crossed, the YES path continues to block 210 in which a determination associated with blood pressure (BP) will require system 100 to intervene by electronically indicating that medication should be administered to the patient. BP of the patient can be measured relative to a systolic threshold level (TS) and/or a diastolic threshold level (TD). TD and/or TS can be the typical normal threshold levels or can be individually established for each patient. A determination is made as to whether BP<TS. If BP is greater than TS, then the NO path continues to block 206 and the method 200 is terminated and the process returns to monitoring for worsening HF conditions in the patient. In contrast, if BP is greater than or equal to TS, then the NO path from block 210 to block 212 causes a first round of medication to be provided to the patient. Administration of a diuretic helps to eliminate water and may reduce blood pressure. To obtain the medication, server 130 is configured to automatically transmit a pre-authorized prescription to the patient. Alternatively, the centralized communication center staffed by a registered nurse contacts the patient to indicate that the medication at a certain dosage should be taken. The prescribed medication is stored in the home of the patient for easy access. The patient then starts taking the prescribed medication. In one embodiment, the medication is a diuretic medication (e.g. furosemide) or vasodilator (e.g. nitrate). Diuretics typically eliminate water from the patient and reduce the blood pressure.

Another determination is made at block 210 as to whether BP<TD. If BP is less than or equal to TD, then the YES path continues to block 206 and the process stops and returns to monitoring for worsening HF conditions in the patient. In contrast, if BP is greater than TD, then the NO path from block 210 to block 212 causes a first round of medication to be provided to the patient, as described above.

At block 214, a determination is made as to whether the patient is experiencing hypotension or extreme weight gain in a short period of time. If the patient is experiencing hypotension, the YES path continues to block 224 in which another determination is made as to whether the patient is experiencing HF symptoms. The YES path from block 224 continues to block 226 that causes the medication to be stopped or terminated. Medication can be stopped for a variety of conditions. Exemplary conditions include the following:

If the patient weighs less than 150 pounds, and the patient's weight changes by 3 pounds per 2 days.

If the patient weighs between 151-300 pounds, and the patient's weight changes by 4 pounds per 2 days.

If the patient weighs greater than 301 pounds, and the patient's weight changes by 5 pounds per 2 days.

One condition requires both a BP condition and the presence of a symptom, as listed immediately below. The BP condition requires the patient exhibit either a systolic blood pressure of the patient is less than 85 mmHg or a diastolic pressure of less than 40 mm Hg. In addition to meeting one of the BP conditions, the patient must be experiencing a symptom that has been conveyed to medical personnel. Exemplary symptoms include (1) recent lightheadedness when moving from sitting to standing positions, or (2) muscle cramping. In addition or alternatively, the physician may customize any one of these conditions to a patient by adding or reducing the weight gain amount or blood pressure level.

Figure 6:
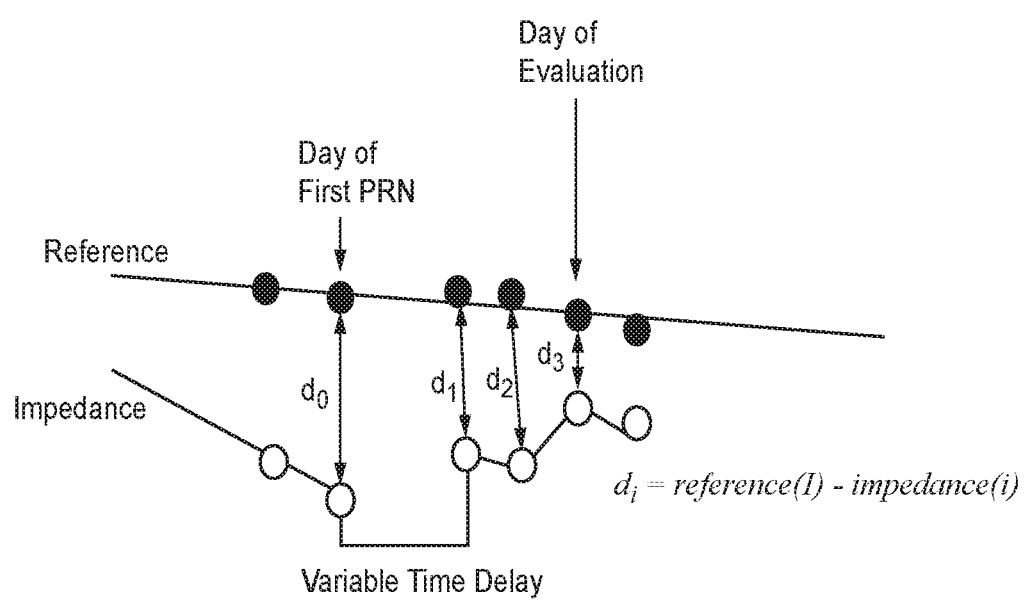
FIG. 6 is a diagram depicting exemplary recovery on a daily basis relative to a reference threshold.

The NO path from blocks 214 and 224 continue to block 216 in which a determination is made as to whether the patient has recovered from his or her worsening HF condition. Exemplary criteria for evaluating PRN efficacy in medication intervention is shown in FIG. 6. Recovery criterion is computed by the server 130 to evaluate PRN efficacy using raw intrathoracic impedance, acquired from IMD 16 associated with the patient, since impedance responds dynamically to patient volume status. Computation of recovery criterion requires the difference to be calculated between raw intrathoracic impedance and the reference impedance. Reference impedance is a component of impedance trend. Daily values for both raw and reference impedance are included with all device diagnostic transmissions spanning a duration of up to 14 months. The difference between raw and reference impedances on pre-specified time period (e.g. four day time period etc.) is required to compute recovery criterion (RC)—the day of PRN initiation ($x_0$), evaluation day ($x_3$), evaluation Day 1 ($x_2$), and evaluation Day 2 ($x_1$), recovery criterion is then computed according to the following equation:

$$RC=100*(x_0-xa)(+x_0-x_2)+(x_0-x_3))/x_0.$$

If the value of RC is greater than a threshold value of 70 (i.e. cumulative impedance recovery over the last 3 days is 70% or more from Day 0 of receiving the initial transmission), the intervention is deemed to be successful. If the value of RC is less than or equal to 70, the intervention is deemed unsuccessful and appropriate follow-up action (i.e. second PRN or notification to the investigator) is taken.

If it is determined at block 216 that the patient has recovered from his worsening HF condition, the YES path continues from block 216 to block 220 in which the patient's status of recovery is stored into memory of server 130. The process is stopped at block 206 and monitoring for worsening HF condition continues. If the patient is not experiencing a recovery, the NO path from block 216 to block 218 requires a patient's blood pressure to be checked and a second round of medication to be initiated. Typically, no additional round of medication is made beyond the second round of medication. Alternatively, a physician prescribed number N can be set of rounds medication can be administrated where N is any number from 1 to 10.

At block 218, another determination is made as to whether the patient is experiencing hypotension or extreme weight gain. The YES path continues from block 222 to block 224, as previously described. The NO path from block 222 to block 228 in which the recovery criteria, described relative to block 216, is repeated. The YES path from block 228 continues to block 230 in which the patient's status of recovery is stored into memory of server 130. The process is stopped 206 and monitoring continues for worsening HF condition.

The NO path from 228 to block 232 requires that the patient be contacted by medical personnel (e.g. nurse) so that a blood sample can be taken for evaluation and confirmation that the proper dosage of medication was provided. Block 240 also requires a blood sample be taken for evaluation and confirmation that the proper dosage of medication was provided.

At block 234, a determination is made as to whether criteria for baseline medications are met. The YES path from block 234 to block 238 requires the health clinic to evaluate and change the baseline medication, if necessary. Exemplary baseline medications along with information that may be useful for medical personnel are presented below.

Baseline Cardiovascular Medication Regimen
BASELINE MEDICATIONS

| Drug Class (Cardiovascular Related e.g. Class Medications) | Drug | Dose and units | Frequency | Route | Reason for use (Medical diagnosis or other reason, e.g. Prophylaxis) |
|---|---|---|---|---|---|
| ACE-inhibitor | ☐ Benazepril (Lotensin)<br>☐ Captopril (Capoten)<br>☐ Enalapril (Vasotec)<br>☐ Fosinopril (Monopril)<br>☐ Lisinopril (Prinivil, Zestril)<br>☐ Moexipril (Univasc)<br>☐ Perindopril (Aceon)<br>☐ Quinapril (Accupril)<br>☐ Ramipril (Altace)<br>☐ Trandolapril (Mavik)<br>☐ Other: _____ | | | | |
| Angiotensin Receptor Blocker | ☐ Candesartan (Atacand)<br>☐ Eprosartan (Teveten)<br>☐ Irbesartan (Avapro)<br>☐ Losartan (Cozaar)<br>☐ Telmisartan (Micardis)<br>☐ Valsartan (Diovan)<br>☐ Other: _____ | | | | |
| Beta blocker (also known as Beta-Adrenergic Blocking agents) | ☐ Acebutolol (Sectral)<br>☐ Atenolol (Tenormin)<br>☐ Betaxolol (Kerlone)<br>☐ Bisoprolol/hydrochlorothiazide (Ziac)<br>☐ Bisoprolol (Zebeta)<br>☐ Metroprolol (Lopressor, Toprol XL)<br>☐ Nadolol (Corgard)<br>☐ Propranolol (Inderal) | | | | |

-continued

Baseline Cardiovascular Medication Regimen
BASELINE MEDICATIONS

| Drug Class (Cardiovascular Related e.g. Class Medications) | Drug | Dose and units | Frequency | Route | Reason for use (Medical diagnosis or other reason, e.g. Prophylaxis) |
|---|---|---|---|---|---|
| | ☐ Sotalol (Betapace) | | | | |
| | ☐ Other: _____ | | | | |
| Combined alpha and beta blockers | ☐ Carvedilol (Coreg) | | | | |
| | ☐ Labetalol hydrochloride (Normodyne, Trandate) | | | | |
| | ☐ Other: _____ | | | | |
| Aldosterone Antagonist | ☐ Spironolactone (Aldactone) | | | | |
| | ☐ Eplerenone (Inspra) | | | | |
| Electrolyte Supplement(s) | ☐ Potassium | | | | |
| | ☐ Magnesium | | | | |
| Vasodilator (Also known as Nitrates) | ☐ Hydralazine (Apresoline) | | | | |
| | ☐ Isosorbide Dinitrate (Isordil) | | | | |
| | ☐ Nesiritide (Natrecor) | | | | |
| | ☐ Nitrates | | | | |
| | ☐ Minoxidil | | | | |
| | ☐ Other: _____ | | | | |
| Anti-arrhythmic Agent | ☐ Amiodarone | | | | |
| | ☐ Other: _____ | | | | |
| Calcium Channel Blocker | ☐ Amlodipine (Norvasc, Lotrel) | | | | |
| | ☐ Diltiazem (Cardizem, Tiazac) | | | | |
| | ☐ Felodipine (Plendil) | | | | |
| | ☐ Nifedipine (Adalat, Procardia) | | | | |
| | ☐ Nimodipine (Nimotop) | | | | |
| | ☐ Nisoldipine (Sular) | | | | |
| | ☐ Verapamil (Calan, Verelan) | | | | |
| | ☐ Other: _____ | | | | |
| Funny Channel ($I_f$) blocker | ☐ Ivabradine (Coriander) | | | | |
| | ☐ Other: _____ | | | | |
| Digitalis Preparation Also known as Digoxin and Digitoxin | ☐ Lanoxin | | | | |
| | ☐ Other: _____ | | | | |
| Other | ☐ _____ | | | | |
| | ☐ _____ | | | | |

Diuretic Regimen
Diuretic Regimen

| Medication (Cardiovascular Related e.g. Class Medications) | Frequency | Route | Titration Stipulations Initiate PRN if baseline dose recently adjusted? |
|---|---|---|---|

BASELINE Diuretic:

☐ Amiloride (Midamor)
☐ Bumetanide (Bumex)
☐ Chlorothiazide (Diuril)
☐ Chlorthalidone (Hygroton)
☐ Furosemide (Lasix)
☐ Hydro-chlorothiazide (Esidrix, Hydrodiuril)
☐ Indapamide (Lozol)
☐ Spironolactone (Aldactone)
☐ Other: _____

BASELINE Diuretic:

☐ Amiloride (Midamor)
☐ Bumetanide (Bumex)
☐ Chlorothiazide (Diuril)
☐ Chlorthalidone (Hygroton)
☐ Furosemide (Lasix)
☐ Hydro-chlorothiazide (Esidrix, Hydrodiuril)
☐ Indapamide (Lozol)

-continued

| Diuretic Regimen |
| --- |
| ☐ Spironolactone (Aldactone)<br>☐ Other: _____<br>BASELINE Diuretic: _____ |
| ☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide (Esidrix, Hydrodiuril)<br>☐ Indapamide (Lozol)<br>☐ Spironolactone (Aldactone)<br>☐ Other: _____ |

Diuretic Regimen for Intervention

| Medication (Cardiovascular Related e.g. Class Medications) | Frequency | Route | Titration Stipulations Initiate PRN if baseline dose recently adjusted? | |
| --- | --- | --- | --- | --- |
| Round 1 PRN:<br>Diuretic<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide (Esidrix, Hydrodiuril)<br>☐ Indapamide (Lozol)<br>☐ Spironolactone (Aldactone)<br>☐ Other: _____<br>And/Or Vasolidilator<br>☐ Hydralazine (Apresoline)<br>☐ Isosorbide Dinitrate Isordil)<br>☐ Nesiritide (Natrecor)<br>☐ Nitrates<br>☐ Minoxidil<br>☐ Other: _____ | RN x 3 days | | ☐ Yes | ☐ No; if baseline dose adjustment made within last ___ days<br>Comment: _____ |
| Round 2 PRN:<br>Diuretic<br>☐ Amiloride (Midamor)<br>☐ Bumetanide (Bumex)<br>☐ Chlorothiazide (Diuril)<br>☐ Chlorthalidone (Hygroton)<br>☐ Furosemide (Lasix)<br>☐ Hydro-chlorothiazide (Esidrix, Hydrodiuril)<br>☐ Indapamide (Lozol)<br>☐ Spironolactone (Aldactone)<br>☐ Other: _____<br>And/Or Vasolidilator<br>☐ Hydralazine (Apresoline)<br>☐ Isosorbide Dinitrate (Isordil)<br>☐ Nesiritide (Natrecor)<br>☐ Nitrates<br>☐ Minoxidil<br>☐ Other: _____ | RN x 3 days | | ☐ Yes | ☐ No; if baseline dose adjustment made within last ___ days<br>Comment: _____ |

If changes to PRN medications are made by a physician, an updated prescription form must be electronically modified in the system 100 and records stored into memory. For example, the updated prescription by the physician can be sent (i.e. faxed, emailed) to system 100, which will automatically update the therapy.

Method 200 is stopped at block 236.

EXEMPLARY EMBODIMENTS OF THE DISCLOSURE

The following embodiments are enumerated consecutively from 1 to 28 provide for various aspects of the present disclosure. In one embodiment, in a first (1) paragraph the present disclosure provides a method for determining whether to intervene with a patient's treatment, the method comprising:

(a) sensing data through an implanted sensor;

(b) using an implanted processor to measure the data against a threshold stored in a memory of an implanted device to determine whether the data is considered to be an HF worsening episode occurrence;

(c) storing the occurrence in the memory of the implanted device;

(d) transmitting the occurrence to an external device;

(e) determining risk status from the occurrence and any other applicable data using the external device;

(f) acquiring additional data from one or more other external devices, the additional data being one of weight, symptoms, and blood pressure; and (g) using the external device to determine whether to adjust treatment of the patient in response to the risk status, the data acquired from the implanted device memory and the one or more other external devices.

A second embodiment is the method according to paragraph 1 further comprising:

storing a treatment plan into the external device's memory, the treatment plan comprising a first round of medication, a second round of medication and/or up to N rounds in which N is any integer.

A third embodiment according to any embodiments 1-2 wherein the treatment plan comprises delivery of a prescribed medication, the prescribed medication adjusted without directly communicating with the patient's physician any time after storing the treatment plan.

A fourth embodiment according to any embodiments of 1-3, further comprising:

displaying the adjusted treatment on a graphical user interface in response to determining that treatment requires adjustment.

A fifth embodiment according to any embodiments of 1-4 further comprising:

acquiring raw impedance data after a prescribed period of time in response to adjusting the treatment of the patient; and using the raw impedance data to determine whether the patient is improving in response to the treatment. Optionally, raw impedance can be used to determine whether the patient is recovering or has recovered.

A sixth embodiment according to any embodiments of 1-5 further comprising: determining whether the raw impedance data, acquired from the implanted device memory, crosses a threshold; in response to determining whether the raw impedance data crosses the threshold, determining whether the raw impedance data is considered a heart failure exacerbation. Optionally, HF exacerbation can mean a treatable HF event.

A seventh embodiment according to any embodiments of 1-6, wherein the raw impedance data that is a non-heart failure exacerbation does not require an intervention by the healthcare system.

A eighth embodiment according to any embodiments of 1-7, wherein the non-heart failure exacerbation does not cause an adjustment to treatment.

A ninth embodiment according to any embodiments of 1-8, wherein the non-heart failure exacerbation triggers a notification to medical personnel.

A tenth embodiment according to any embodiments of 1-9, wherein the non-heart failure exacerbation does not trigger an intervention.

An eleventh embodiment according to any embodiments of 1-10, wherein the raw impedance data that is a heart failure exacerbation that requires an intervention by the healthcare system.

A twelfth embodiment according to any embodiments of 1-11 further comprising:

determining whether to terminate adjusted treatment in response to data monitored after treatment was adjusted.

A thirteenth embodiment according to any embodiments of 1-12, wherein termination of adjusted treatment is based upon one of patient blood pressure, and/or symptoms.

A fourteenth embodiment according to any embodiments of 1-13 further comprising: generating a notification for delivery of a first round of medication.

A fifteenth embodiment according to any embodiments of 1-14, further comprising: generating a notification for delivery of a second round of medication.

A sixteenth embodiment according to any embodiments of 1-15, further comprising: monitoring one of the implanted device memory data and the external device data after delivery of one of a first or a second round of medication.

A seventeenth embodiment according to according to any embodiments of 1-16, further comprising:

generating a notification to one of medical personnel and a patient for a blood sample to be acquired and tested.

A eighteenth embodiment according to any embodiments of 1-17 further comprising: adjusting therapy in response determining weight loss.

A nineteenth embodiment according to any embodiments of 1-17 further comprising: adjusting therapy in response determining blood pressure and/or a symptom.

A twentieth embodiment according to any embodiments of 1-19 wherein the symptom related to one of lightheadedness and muscle cramping.

A twenty first embodiment according to any embodiments of 1-20 wherein the adjusted therapy involves cessation of one or more medications.

A twenty second embodiment according to any of embodiments 1-21 wherein the adjusted therapy involves one or more medications being increased in dosage.

A twenty third embodiment according to any embodiments of 1-22 wherein one or more baseline medications are examined.

A twenty fourth embodiment according to any embodiments of 1-23 further comprising: determining whether one of a set criteria has been met; and triggering review of one or more baseline medications in response to determining whether one of a set criteria has been met.

A twenty fifth embodiment according to any embodiments of 1-24 wherein the one of the set criteria comprises:

(a) average pre-specified time period impedance is less a threshold;

(b) two or more medication interventions occurred within a pre-specified amount of time; and (c) two or more medication interventions were administered to the patient.

A twenty sixth embodiment according to any embodiments of 1-25 wherein the threshold for the average pre-specified time period impedance is less than or about less than 66 Ohms.

A twenty seventh embodiment according to any embodiments of 1-26 wherein the pre-specified time period is about three months.

A twenty eighth embodiment wherein the treatment plan comprises medication as a transient increase in diuretic or vasodilator. Transient increase in medication means that a nominal amount of diuretic or vasodilator can be made without approval from a physician.

A twenty eighth embodiment involving a method for determining whether to intervene with a patient's treatment, the method comprising:

(a) sensing data through an implanted sensor;

(b) using an implanted processor of an implanted device to measure the data against a threshold stored in a memory of the implanted device to determine whether the data is considered to be a HF worsening episode occurrence;

(c) storing the occurrence in the memory of the implanted device;
(d) transmitting from the implanted device the occurrence to an external device;
(e) using the external device to determine the risk status from the occurrence and any other applicable data;
(f) acquiring additional data, by the external device, from one or more other external devices, the additional data being one of weight, symptoms, and blood pressure; and
(g) using the external device to determine whether to adjust the patient's treatment in response to the risk status, the data acquired from the implanted device memory and the one or more other external devices.

A twenty ninth embodiment of a system for determining whether to intervene with a patient's treatment, the system comprising:
an implantable device having a memory;
an implantable sensor;
an implantable processor;
an external device;
sensing means for sensing data through the implanted sensor;
the implanted processor configured to compare the data against a threshold stored in the memory of the implanted device to determine whether the data is considered to be indicative of a heart failure (HF) worsening episode occurrence based on a result of the comparison;
storing means for storing a determined occurrence in the memory of the implanted device;
transmitting means for transmitting the occurrence to the external device;
processing means for determining a risk status from the occurrence and any other applicable data using the external device;
means for acquiring additional data, the additional data being one of weight, symptoms, and blood pressure; and
the external device configured to determine whether to adjust the patient's treatment based on the risk status, the data acquired from the implanted device memory and the one or more other external devices.

A thirtieth embodiment of a system of embodiment 29 wherein the additional data is acquired from the external device or one or more other external devices.

A thirty first embodiment of a system of embodiment 29 or 30 wherein the additional data related to the blood pressure is acquired from the implantable processor, another implantable processor associated with another implantable device, and a wireless pulmonary artery sensor. An example of such a wireless pulmonary artery sensor located in the pulmonary artery is found in U.S. patent application Ser. No. 15/378,989, filed Dec. 14, 2016, and assigned to the assignee of the present invention, the disclosure of which is incorporated by reference in its entirety herein. The wireless pulmonary artery sensor is configured to wirelessly communicate with other implantable medical devices for monitoring and/or storing sensed physiological data such as LINQ™. LINQ™ can then wirelessly communicate data to an external device such as a portable device (e.g. iPhone, computer) or to the external device such as server 130. Tissue conductance communication is used to communicate between the wireless pulmonary artery sensor and LINQ™. An exemplary implantable monitoring device is found in US Patent Publication No. US 2016-0310031 A1, filed Apr. 20, 2016 to Sarkar, and assigned to the assignee of the present invention, the disclosure of which is incorporated by reference in its entirety herein A thirty second embodiment of a system according to one of embodiments 29-31 wherein the additional data related to the blood pressure is acquired from the external device or one or more external devices.

A thirty second embodiment of a system according to one of embodiments 29-32 wherein the implanted sensor is mechanically and electrically connected to the implanted device.

A thirty third embodiment of a system according to one of embodiments 29-33 wherein the implanted sensor is not mechanically connected to the implanted device.

A thirty fourth embodiment of a system according to one of embodiments 29-34 further comprising:
storing means for storing a treatment plan into a memory of the external device, the treatment plan comprising a first round of medication and a second round of medication.

A thirty fifth embodiment of a system according to one of embodiments 29-34 wherein the treatment plan comprises delivery of a prescribed medication, the prescribed medication adjusted without directly communicating with the patient's physician any time after storing the treatment plan into memory.

A thirty sixth embodiment of a system according to one of embodiments 29-35, further comprising:
displaying means for displaying the adjusted treatment on a graphical user interface in response to determining that the patient's treatment requires adjustment.

A thirty seventh embodiment of a system according to one of embodiments 29-36 further comprising:
means for acquiring raw impedance data after a prescribed period of time in response to adjusting the treatment of the patient; and
means for using the raw impedance data to determine whether the patient is improving in response to the treatment.

A thirty eighth embodiment of a system according to one of embodiments 29-37, further comprising:
processing means for determining whether the raw impedance data, acquired from the implanted device memory, crosses a threshold; and
in response to determining whether the raw impedance data crosses the threshold, determining whether the raw impedance data is considered a heart failure exacerbation.

A thirty ninth embodiment of a system according to one of embodiments 29-38, wherein the raw impedance data that is a non-heart failure exacerbation does not require an intervention by the healthcare system.

A fortieth embodiment of a system according to one of embodiments 29-39, wherein the non-heart failure exacerbation does not cause an adjustment to treatment.

A forty first embodiment of a system according to one of embodiments 29-40, wherein the non-heart failure exacerbation triggers a notification to medical personnel.

A forty second embodiment of a system according to one of embodiments 29-41, wherein the non-heart failure exacerbation does not trigger an intervention.

A forty third embodiment of a system according to one of embodiments 29-42, wherein the raw impedance data that is a heart failure exacerbation that requires an intervention by the healthcare system.

A forty fourth embodiment of a system according to one of embodiments 29-43, further comprising:

processing means for determining whether to terminate adjusted treatment in response to data monitored after treatment was adjusted.

A forty fifth embodiment of a system according to one of embodiments 29-44, wherein termination of adjusted treatment is based upon one of patient blood pressure, and symptoms. The external device may be a server 130. Another external device may be another computer or server.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A method of delivering diuretic medication therapy to a patient using a computer system, comprising:
   storing a treatment plan defining a first round of diuretic medication therapy;
   using the computer system to determine that the patient is suffering from a worsening heart failure (HF) condition;
   after using the computer system to determine that the patient is suffering from the worsening HF condition, determining that the patient has a blood pressure that is above a defined threshold;
   in response to the determination that the patient is suffering from the worsening HF condition and the patient's blood pressure is above the defined threshold, initiating the first round of diuretic medication therapy without first contacting a physician;
   thereafter determining whether the patient has undergone a weight change in excess of a defined amount of weight over time;
   in response to the determination that the patient has undergone the weight change in excess of the defined amount of weight over time, determining whether the patient is also experiencing a specific HF symptom;
   in response to the determination that the patient is also experiencing the specific HF symptom, stopping delivery of the first round of diuretic medication therapy; and
   thereafter using the computer system to monitor the patient for the worsening HF condition.

2. The method of claim 1 wherein the step of initiating the first round of diuretic medication therapy comprises using the computer system to provide the patient with a pre-authorized prescription for the first round of diuretic medication therapy.

3. The method of claim 1 wherein the patient has the first round of diuretic medication therapy on-hand and wherein the step of initiating the first round of diuretic medication therapy comprises contacting the patient to indicate that the first round of diuretic medication therapy should be initiated.

4. The method of claim 1 wherein using the computer system to determine that the patient is suffering from the worsening HF condition comprises providing the computer system with diagnostic data and using the computer system to analyze the diagnostic data to determine that the patient is at an increased risk of the worsening HF condition and thereafter confirming that the patient is in the worsening HF condition by communicating with the patient to determine that the worsening HF condition is in fact present.

5. The method of claim 4 wherein the step of communicating with the patient comprises asking the patient a series of questions.

6. The method of claim 1, further comprising:
   in response to the determination that the patient has not undergone the weight change in excess of the defined amount of weight over time, using the computer system to determine whether the patient has recovered from the worsening HF condition.

7. The method of claim 6, wherein the treatment plan further defines a second round of diuretic medication therapy, the method further comprising initiating the second round of diuretic medication therapy without first contacting the physician in response to the determination that the patient has not recovered from the worsening HF condition.

8. The method of claim 6, further comprising stopping the first round of diuretic medication therapy in response to the determination that the patient has recovered from the worsening HF condition.

9. The method of claim 6 wherein the step of determining whether the patient has recovered comprises using the computer system to analyze the patient's transthoracic impedance over a series of days.

10. The method of claim 9 wherein the patient is determined to have recovered in response to the analysis of the patient's transthoracic impedance indicating a return to within a defined percentage of a reference impedance.

11. A method of delivering diuretic medication therapy to a patient using a computer system, comprising:
   storing a treatment plan defining a first round of diuretic medication therapy;
   using the computer system to determine that the patient is suffering from a worsening heart failure (HF) condition;
   after using the computer system to determine that the patient is suffering from the worsening HF condition, determining that the patient has a blood pressure that is above a defined threshold;
   in response to the determination that the patient is suffering from the worsening HF condition and the patient's blood pressure is above the defined threshold, initiating the first round of diuretic medication therapy without first contacting a physician;
   thereafter determining whether the patient has undergone a weight change in excess of a defined amount of weight over time;
   in response to the determination that the patient has undergone the weight change in excess of the defined amount of weight over time, determining whether the patient is also experiencing a specific HF symptom; and
   in response to the determination that the patient has not undergone the weight change in excess of the defined amount of weight over time, using the computer system to determine whether the patient has recovered from the worsening HF condition.

12. The method of claim 11, wherein the treatment plan further defines a second round of diuretic medication therapy, the method further comprising initiating the second round of diuretic medication therapy without first contacting the physician in response to the determination that the patient has not recovered from the worsening HF condition.

13. The method of claim 11, further comprising stopping the first round of diuretic medication therapy in response to the determination that the patient has recovered from the worsening HF condition.

14. The method of claim 11 wherein the step of determining whether the patient has recovered comprises using the computer system to analyze the patient's transthoracic impedance over a series of days.

15. The method of claim 14 wherein the patient is determined to have recovered in response to the analysis of the patient's transthoracic impedance indicating a return to within a defined percentage of a reference impedance.

16. The method of claim 11 wherein the step of initiating the first round of diuretic medication therapy comprises using the computer system to provide the patient with a pre-authorized prescription for the first round of diuretic medication therapy.

17. The method of claim 11 wherein the patient has the first round of diuretic medication therapy on-hand and wherein the step of initiating the first round of diuretic medication therapy comprises contacting the patient to indicate that the first round of diuretic medication therapy should be initiated.

18. The method of claim 11 wherein using the computer system to determine that the patient is suffering from the worsening HF condition comprises providing the computer system with diagnostic data and using the computer system to analyze the diagnostic data to determine that the patient is at an increased risk of the worsening HF condition and thereafter confirming that the patient is in the worsening HF condition by communicating with the patient to determine that the worsening HF condition is in fact present.

19. The method of claim 18 wherein the step of communicating with the patient comprises asking the patient a series of questions.

* * * * *